United States Patent
Hammen et al.

(10) Patent No.: US 12,214,177 B2
(45) Date of Patent: Feb. 4, 2025

(54) FLEXIBLE MODULES FOR INJECTION DEVICES

(71) Applicant: Sanofi-Aventis Deutschland GmbH, Frankfurt am Main (DE)

(72) Inventors: Dietmar Hammen, Frankfurt am Main (DE); Thomas Klemm, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 378 days.

(21) Appl. No.: 17/872,795

(22) Filed: Jul. 25, 2022

(65) Prior Publication Data

US 2023/0011040 A1    Jan. 12, 2023

Related U.S. Application Data

(63) Continuation of application No. 16/480,840, filed as application No. PCT/EP2018/051811 on Jan. 25, 2018, now Pat. No. 11,524,122.

(30) Foreign Application Priority Data

Jan. 26, 2017    (EP) .................................... 17153398

(51) Int. Cl.
   *A61M 5/315*    (2006.01)
   *A61M 5/24*    (2006.01)
   *A61M 5/31*    (2006.01)

(52) U.S. Cl.
   CPC .......... *A61M 5/31593* (2013.01); *A61M 5/24* (2013.01); *A61M 5/31585* (2013.01);
   (Continued)

(58) Field of Classification Search
   CPC .......... A61M 5/31585; A61M 5/31593; A61M 5/31525; A61M 5/31568; A61M 5/24;
   (Continued)

(56) References Cited

U.S. PATENT DOCUMENTS

| 7,965,180 B2 | 6/2011 | Koyama |
| 9,197,082 B1 | 11/2015 | Zhang |

(Continued)

FOREIGN PATENT DOCUMENTS

| CN | 2728513 | 9/2005 |
| CN | 104066467 | 9/2014 |

(Continued)

OTHER PUBLICATIONS

International Preliminary Report on Patentability in Application No. PCTEP2018051811, dated Jul. 30, 2019, 8 pages.

(Continued)

*Primary Examiner* — Tasnim Mehjabin Ahmed
(74) *Attorney, Agent, or Firm* — Fish & Richardson P.C.

(57) ABSTRACT

Implementations of the present disclosure are directed to a module for attachment to an injection device that includes a flexible carrier foil configured to be attached to a surface of the injection device independent of a geometry of the surface, at least one light emitting diode attached to the flexible carrier foil in a first position and configured to emit a light signal in a direction based on the first position through a transparent wall of the injection device, at least one photodiode attached to the flexible carrier foil in a second position relative to the first position, the at least one photodiode being configured to detect at least a portion of the light signal from a direction based on the second position and being configured to emit an electrical signal based on the light signal to a microprocessor, and wherein the microprocessor is configured to receive the electrical signal emitted by the photodiode and to determine the position of a stopper and the amount of the fluid within the injection device based at least in part on the electrical signal.

20 Claims, 9 Drawing Sheets

(52) U.S. Cl.
CPC . *A61M 2005/3126* (2013.01); *A61M 5/31525* (2013.01); *A61M 5/31568* (2013.01); *A61M 2205/50* (2013.01); *A61M 2205/58* (2013.01)

(58) Field of Classification Search
CPC ...... A61M 5/31528; A61M 2005/3126; A61M 2205/50
See application file for complete search history.

(56) References Cited

U.S. PATENT DOCUMENTS

| | | | |
|---|---|---|---|
| 11,524,122 B2 * | 12/2022 | Hammen | A61M 5/31593 |
| 2005/0038332 A1 | 2/2005 | Saidara et al. | |
| 2011/0313395 A1 | 12/2011 | Krulevitch et al. | |
| 2012/0268741 A1 | 10/2012 | Pommereau et al. | |
| 2013/0161985 A1 | 6/2013 | Fukawatase | |
| 2013/0324920 A1 * | 12/2013 | Kohli | A61M 5/19 604/84 |
| 2015/0048836 A1 | 2/2015 | Guthrie et al. | |
| 2016/0008541 A1 | 1/2016 | Hirschel et al. | |
| 2016/0161985 A1 | 6/2016 | Zhang | |
| 2017/0055890 A1 | 3/2017 | Kube et al. | |
| 2017/0331309 A1 | 11/2017 | Gofman et al. | |
| 2017/0347927 A1 | 12/2017 | He | |
| 2020/0275867 A1 | 9/2020 | Klemm | |
| 2021/0080451 A1 | 3/2021 | Klemm | |

FOREIGN PATENT DOCUMENTS

| | | | |
|---|---|---|---|
| CN | 105209091 | 12/2015 | |
| EP | 2190504 | 1/2014 | |
| JP | 2013-135557 | 7/2013 | |
| JP | 2015-518747 | 7/2015 | |
| JP | 2017-505648 | 2/2017 | |
| JP | 2017-196423 | 11/2017 | |
| WO | WO 2009/032402 | 3/2009 | |
| WO | WO 2013/063634 | 5/2013 | |
| WO | WO 2013/085453 | 6/2013 | |
| WO | WO 2013/177135 | 11/2013 | |
| WO | WO 2014/184080 | 11/2014 | |
| WO | WO 2015/102740 | 7/2015 | |
| WO | WO 2015/136564 | 9/2015 | |
| WO | WO 2016/019375 | 2/2016 | |
| WO | WO 2016/055400 | 4/2016 | |
| WO | WO 2016/110592 | 7/2016 | |
| WO | WO 2016/142216 | 9/2016 | |
| WO | WO 2016/166338 | 10/2016 | |
| WO | WO-2016166338 A1 * | 10/2016 | A61J 1/22 |

OTHER PUBLICATIONS

International Search Report and Written Opinion in Application No. PCTEP2018051811, dated Feb. 27, 2018, 12 pages.
Freudenthal et al., "Suitability of NFC for Medical Device Communication and Power Delivery," IEEE Dallas Engineering in Medicine and Biology Workshop, Nov. 11, 2007, pp. 51-54.

* cited by examiner

FLEXIBLE MODULES FOR INJECTION DEVICES

CROSS REFERENCE TO RELATED APPLICATIONS

The present application is a continuation of U.S. application Ser. No. 16/480,840, filed on Jul. 25, 2019, which is the national stage entry of International Patent Application No. PCT/EP2018/051811, filed on Jan. 25, 2018, and claims priority to Application No. EP 17153398.7, filed on Jan. 26, 2017, the disclosures of which are incorporated herein by reference.

FIELD

This disclosure relates to modules for injection devices. In particular, the disclosure relates to flexible modules for determining the amount of a fluid within an injection device.

BACKGROUND

A variety of diseases exist that require treatment by injection of a medicament. Such injection can be performed using injection devices, which are applied either by medical personnel or by patients themselves. As an example, type-1 and type-2 diabetes can be treated by patients themselves by injection of insulin doses, for example once or several times per day. For instance, a pre-filled disposable insulin pen or autoinjector can be used as an injection device. Alternatively, a re-usable pen or autoinjector may be used. A re-usable pen or autoinjector allows replacement of an empty medicament cartridge by a new one. Either type of pen or autoinjector may come with a set of one-way needles that are replaced before each use. Labels including transceivers and responders in the form of so-called smart labels (e.g., intelligent labels) are used in many areas of technology. In contrast to conventional labels, for example printed and purely optically readable labels, the information associated with smart labels can be transmitted electronically. In addition, a visible surface of the smart label can also be inscribed, for example printed on or inscribed, in order to apply optically discernible information.

These properties of smart labels are exploited, for example, in the tracking of goods in the haulage industry, in products logistics, in the area of protection against theft, in the battle against counterfeit goods, in healthcare continuum and in other areas of technology. For example, the US Food and Drug Agency recommends the use of radio frequency identification (RFID) techniques in the battle against counterfeit medicines. Additionally, temperature-sensitive medicaments are often used with smart labels including a sensor function on the transport containers. The temperature recording can, for example, document a breach of transport conditions and can therefore protect patients against illegally transported pharmaceuticals or medical products. Smart labels attached to medical injection devices can also be used to share information regarding the operation of an injection device with healthcare providers. The sharing of medical information using smart labels can result in healthcare optimizations and improvements.

SUMMARY

Implementations of the present disclosure include flexible modules and systems configured for sharing data in a healthcare continuum, the data being determined by a flexible smart label (module) and corresponding to an amount of fluid within an injection device the flexible smart label is associated therewith. In accordance with one aspect of the present invention, a flexible module can include a flexible carrier foil configured to be attached to a surface of the injection device independent of a geometry of the surface, at least two light emitting diodes attached to the flexible carrier foil in a first position and configured to emit a light signal in a direction based on the first position through a transparent wall of the injection device, at least two photodiodes attached to the flexible carrier foil in a second position relative to the first position, the at least two photodiodes being configured to detect a portion of the light signal reflected by a plunger of the injection device in a direction of the second position and the at least two photodiodes being configured to emit an electrical signal based on the reflected light signal, wherein the plunger is configured to expel a portion of a fluid, such that a stopper position is associated with an amount of the fluid within the injection device, and a microprocessor configured to determine the amount of the fluid within the injection device based at least in part on the electrical signal.

In some implementations, the portion of the surface can define a non-planar geometry. The portion of the surface can be substantially curved. The microprocessor can be silicon based and configured to maintain an elasticity of the module. The first position and the second position can be on opposite sides of the injection device. The stopper position can be determined based on a barrier principle. The first position and the second position define a line that can be substantially parallel to a longitudinal axis of the injection device. The stopper position can be determined based on a reflective principle. The stopper can be configured to reflect the light signal. The module can include a power source configured to maintain the elasticity of the flexible module. The power source includes at least one of an integrated flexible battery or super capacitor.

In other implementations, the module can include a near-field communication (NFC) antenna having a structure configured to maintain the elasticity of the flexible module, the NFC antenna being configured to harvest energy for the power source and being configured to transmit the amount of the fluid to an external processor. The external processor can be configured to perform operations including: display the amount of the fluid within the injection device and receiving a user input indicating a dose to be delivered by the injection device. The NEC antenna can be configured to transmit the amount of the fluid at a time interval. The module can include a temperature sensor configured to maintain the elasticity of the flexible module. The module can include an adhesive layer. The module can include a mechanical protection layer. The module can include a digital display configured to display the amount of the fluid within the injection device.

In accordance with another aspect of the present invention, a fluid delivery system can include an injection device configured to store and dispense a fluid, the injection device having light transparent walls and including a plunger configured to expel a portion of the fluid, such that a stopper position can be associated with an amount of the fluid within the injection device, and a flexible module configured to attach to a surface of the injection device independent of a geometry of the surface, the flexible module including: a carrier foil configured to be attached to the surface, at least two light emitting diodes attached to the carrier foil in a first position and configured to emit a light signal in a direction based on the first position, at least two photodiodes attached to the carrier foil in a second position relative to the first position, the at least two photodiodes being configured to detect the light signal from a direction based on the second position and being configured to emit an electrical signal based on the light signal, and a microprocessor configured to determine the amount of the fluid within the injection device based on the electrical signal.

In accordance with yet another aspect of the present invention, a module for removable attachment to a fluid reservoir of an injection device can include: a flexible carrier foil configured to be attached to a surface of the fluid reservoir independent of a geometry of the surface, at least two light emitting diodes attached to the carrier foil in a first position and configured to emit a light signal in a direction based on the first position through a transparent wall of the fluid reservoir, at least two photodiodes attached to the carrier foil in a second position relative to the first position, the at least two photodiodes being configured to detect a portion of the light signal reflected by a plunger of the injection device in a direction of the second position and the at least two photodiodes being configured to emit an electrical signal based on the reflected light signal, wherein the plunger can be configured to expel a portion of the fluid, such that a stopper position can be associated with an amount of the fluid within the injection device, and a microprocessor configured to determine the amount of the fluid within the injection device based on the electrical signal.

In accordance with yet another aspect of the present invention, a method to detect an amount of fluid in a reservoir of an injection device by performing operations including: attaching a flexible carrier foil to a surface of the fluid reservoir independent of a geometry of the surface, generating a light signal by at least two light emitting diodes attached to the carrier foil in a first position, the light signal being directed in a direction based on the first position through a transparent wall of the fluid reservoir, receiving a portion of the light signal reflected by a stopper of the injection device by at least two photodiodes attached to the carrier foil in a second position relative to the first position, emitting an electrical signal based on the reflected light signal by the at least two photodiodes, and determining by a microprocessor the amount of the fluid within the injection device based on the electrical signal.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

DESCRIPTION OF DRAWINGS

FIGS. 10-1E are schematic diagrams depicting examples of devices in accordance with the present disclosure.

Like reference symbols in the various drawings indicate like elements.

DETAILED DESCRIPTION

Flexible modules (e.g., flexible smart labels) can be attached to a surface of an injection device and facilitate sharing of medical data. For example, a healthcare provider may optimize healthcare treatment, avoid usage of expired or incorrectly stored medicaments, and avoid shortage of medical supply by attaching a flexible smart labels to injection devices to continuously monitor a plurality of parameters associated with a fluid medical product (sometimes referred to as a medicament) that is contained within the injection devices and delivered by the injection devices. The data including the amount of fluid that is contained within the injection devices and delivered by the injection devices can be shared with one of more healthcare providers and other entities within a healthcare continuum (e.g., a system that supports, guides, and tracks medical treatment of patients over time through a comprehensive array of health services spanning all levels and intensity of care) that may use the information (e.g., to replenish the medical supply).

Figure 1A:
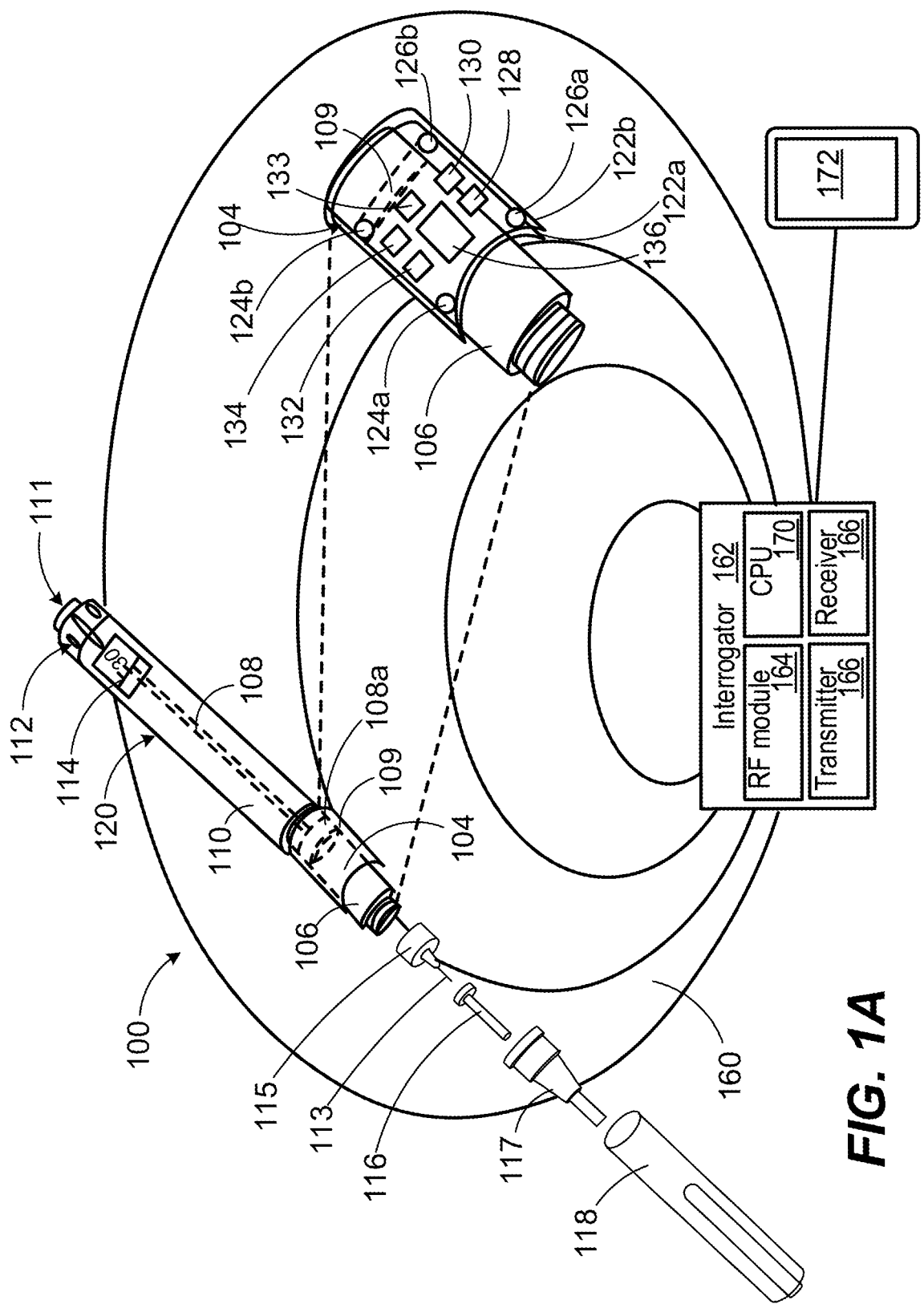
FIGS. 1A and 1B are exploded views of examples of devices in accordance with the present disclosure.
Figure 1B:
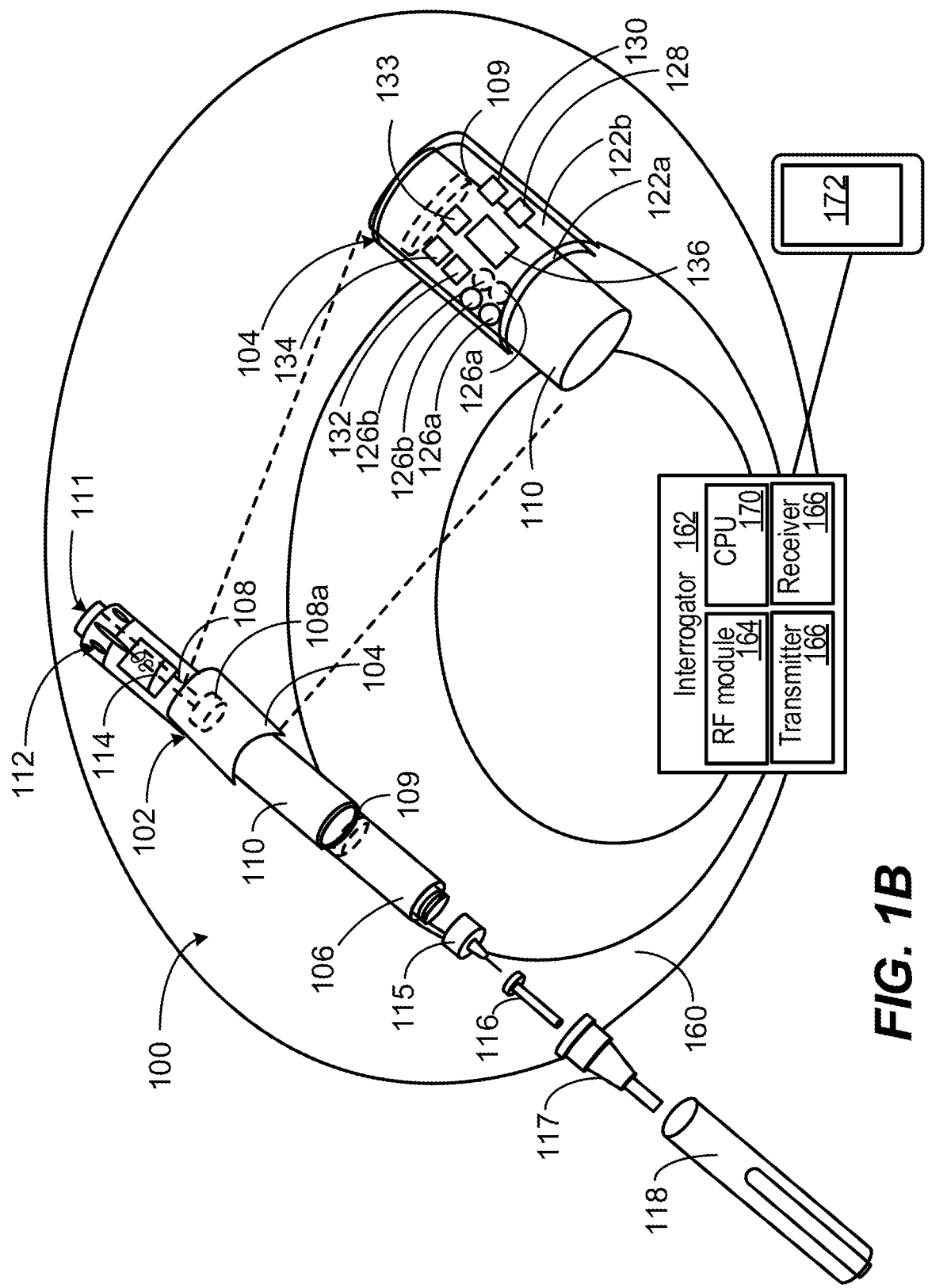

FIGS. 1A and 1B illustrate exploded views of example fluid delivery systems 100 including an injection device 102 with a flexible smart label 104 that can be used to share data across a healthcare continuum. In FIG. 1A, the flexible smart label 104 is attached to a cartridge 106. In FIG. 1B, the flexible smart label 104 is attached to a surface of a housing 110 of the injection device 102. The injection device 102 can be a pre-filled, disposable injection pen or the injection device 102 can be a reusable injection pen. The injection device 102 can include the housing 110 and contains the cartridge 106, to which a needle assembly 115 that includes a needle 113 can be affixed. A portion of the housing and/or the cartridge 106 are made of materials (e.g., glass) that are transparent for light beams in visible and infrared spectrum.

The needle is protected by an inner needle cap 116 and an outer needle cap 117, which in turn can be covered by a cap 118. The cartridge 106 can be configured to contain a fluid medicament. A dose of the contained medicament can be ejected from the injection device 102 by turning the dosage knob 112, and the selected dose is then displayed via dosage window 114, for instance in multiples of so-called International Units (IU), wherein one IU is the biological equivalent of about 45.5 micrograms of pure crystalline insulin (1/22 mg). An example of a selected dose displayed in dosage window 114 may for instance be 30 IUs, as shown in FIG. 1A. In some implementations, the selected dose can be displayed differently, for instance by an electronic display (e.g., the dosage window 114 may take the form of an electronic display).

Turning the dosage knob 112 can cause a mechanical click sound to provide acoustical feedback to a user. The numbers displayed in dosage window 114 can be printed on a sleeve that is contained in housing 110 and mechanically interacts with a plunger head 108a that is fixed at the end of the screw 108 and pushes the stopper 109 of the cartridge 106. The plunger head 108a is configured to expel a portion of the fluid by displacing the stopper 109 contained within the cartridge 106, such that a position of the stopper 109 is associated with an amount of the fluid within the injection device 102. When needle 115 is stuck into a skin portion of a patient, and then injection button 111 is pushed, the insulin dose displayed in display window 114 can be ejected from injection device 102. When the needle 115 of injection device 102 remains for a certain time in the skin portion after the injection button 111 is pushed, a high percentage of the dose is actually injected into the patient's body. Ejection of the insulin dose can generate a mechanical click sound, which can be different from the sounds produced when using dosage knob 112. As described in further detail below, the flexible smart label 104 can include an adhesive layer 122a and a carrier layer (or carrier foil) 122b. The carrier layer/foil 122b can include electronic components such as LEDs and photodiodes that can be used to sense characteristics of the injection device 102 such as the stopper position and/or amount of medicament in the cartridge 106. The flexibility and the adhesive can allow the module to be attached to injection devices of differing dimensions, e.g. varying diameters.

Injection device 102 may be used for several injection processes until either cartridge 106 is empty or the expiration date of injection device 102 (e.g. 28 days after the first use) is reached. Before using injection device 102 for the first time, it may be necessary to perform a so-called "prime shot" to remove air from cartridge 106 and needle 115, for instance by selecting two units of insulin and pressing injection button 111 while holding injection device 102 with the needle 115 upwards.

The flexible smart label 104 can be configured to attach to a variety of surface geometries, including planar and non-planar geometries (e.g., curved, angled or a combination thereof) to continuously or periodically monitor the amount of fluid that is contained within the injection device 102 and delivered by the injection device 102. The flexible smart label 104 can be associated with an identifier. The identifier can be a random number r that can be encoded in a machine-readable medium, such as radio frequency identification (RFID) data, in a 2-dimensional (2D) bar code, and/or in a QR code included with the item. The random number r can be associated with the flexible smart label 104 and can be used to uniquely identify the flexible smart label 104 and corresponding flexible smart label-level data stored in a repository.

The flexible smart label 104 can be configured to possess enhanced mechanical, thermal, electrical, optical, and physical properties such as flexibility, surface hardness, thermal conductivity, dielectric constant, abrasion resistance, optical transmissivity, permeability, chemical stability, bond strength, and other properties. For example, the flexible smart label 104 can have a Young's Modulus of from about 0.5 to about 5 GPa, a dielectric constant of from about 2 to about 5, and a Rockwell hardness of from about 35 to about 120. The flexible smart label 104 can include an adhesive layer 122a and a carrier layer/foil 122b. The adhesive layer 122a can be configured to removably attaching the flexible smart label to a surface of the injection device 102. The adhesive layer 122a can be urethane resin-based, silicone resin-based, vinyl resin-based, polyester resin-based, synthetic rubber-based, and natural rubber-based adhesives, etc. In some implementations, the adhesive layer can include a non-attachable corner to enable the removal of the flexible smart label 104 from the injection device 102.

A plurality of flexible components can be attached to the carrier layer/foil 122b. The flexible components can include printed electronics generated using functional inks for printing the electronics defining the flexible smart label 104. The plurality of flexible components includes light emitting diodes (LEDS) 124a and 124b, photodiodes 126a and 126b, a microprocessor 128, an antenna 130, a temperature sensor 132, a power source 134, and a display 136. The LEDS 124a and 124b can have a variety of geometries, such as circles, rectangles and/or stripes (having one side significantly larger than the other side). In some implementations, a single LED 124a can be used. The single LED can be a stripe. In other implementations, multiple LEDS 124a and 124b can be arranged as an array of LEDS, including at least two LEDS. The array of LEDS 124a and 124b can be a linear array or a rectangular array.

The LEDS 124a and 124b can be attached to the carrier foil in a first position that can define a longitudinal (FIG. 1A) or a radial (FIG. 1B) arrangement of the LEDS 124a and 124b. The LEDS 124a and 124b can be configured to emit a light signal in a direction based on the first position towards the photodiodes 126a and 126b through an optically transparent wall of the cartridge 106 (FIG. 1A) or of the housing 110 (FIG. 1B). In some implementations, LEDS 124a and 124b can emit an invisible light signal (e.g., in infrared spectrum).

The photodiodes 126a and 126b can be have a variety of geometries, such as rectangles and/or stripes (having one side significantly larger than the other side). The circular and rectangular photodiodes 126a and 126b can have a pixel size of tens of μm. The stripe photodiode can have a length in the order of millimeters that is shorter than the length of the screw 108 or the cartridge 106. In some implementations, a single photodiode can be used. The single photodiode 126a can be a stripe (e.g., autoinjector). In other implementations, multiple photodiodes 126a and 126b can be arranged in a row or as an array of photodiodes, including at least two photodiodes (e.g., four, six or hundreds photodiodes). The photodiodes 126a and 126b can be arranged in a regular pattern with equal distances between the photodiodes. The photodiodes 126a and 126b can be arranged in an irregular pattern that can have two distances between the photodiodes, one of the distances being half of the other distance to increase the detection accuracy.

The photodiodes 126a and 126b are attached to the carrier foil in a second position relative to the first position of the LEDS 124a and 124b and can define a longitudinal (FIG. 1A) or a radial (FIG. 1B) arrangement of the photodiodes 126a and 126b. The arrangement and sizes of each of the LEDS 124a and 124b and each of the photodiodes 126a and 126b can be based on a desired illumination pattern. The arrangement and sizes of the LEDS 124a and 124b and the photodiodes 126a and 126b can depend on one or more characteristics of the injection device 102 (e.g., geometry, size, transparency to light emitted by LEDS 124a and 124b, etc.) and aimed resolution and accuracy of data associated with the amount of fluid within the cartridge (e.g., drug unit level).

For example, the first and second positions can be selected such that LEDS 124a and 124b and photodiodes 126a and 126b are placed on opposite sides of the cartridge 106 (FIG. 1A) or of the housing 110 to determine the amount of medicament based on barrier principle. Within the context example, the light signal generated by the LEDS 124a and 124b does not intersect the stopper 109 when the cartridge 106 is full (e.g., each photodiode 126a and 126b receives a light signal), intersects a portion of the stopper 109 when the cartridge 106 is partially full (e.g., at least one photodiode at a first known position does not receive a light signal), and a second portion or substantially all light signal intersects the stopper 109 when the cartridge 106 is empty (e.g., at least one photodiode at a second known position does not receive a light signal).

As another example, the first and second positions can be selected such that LEDS 124a and 124b and photodiodes 126a and 126b are placed on the same side, in partially overlapping sides or on separate sides of the cartridge 106 or of the housing 110 (FIG. 1B) to determine the amount of medicament based on a reflective principle. Within the context example, the light signal generated by the LEDS 124a and 124b is mostly or substantially completely reflected by the stopper 109 when the cartridge 106 is full (e.g., each photodiode 126a and 126b receives a light signal), is partially reflected away from the photodiodes 126a and 126b by the stopper 109 when the cartridge 106 is partially full (e.g., at least one photodiode at a first known position does not receive a light signal), and is partially or substantially completely reflected away from the photodiodes 126a and 126b by the stopper 109 when the cartridge 106 is empty (e.g., at least one photodiode at a second known position does not receive a signal). The photodiodes 126a and 126b can be configured to detect the light signal that reaches the second position after being absorbed or reflected by the stopper 109. The stopper 109 can be configured to be optically absorbent (e.g., made of black material) or reflective. The photodiodes 126a and 126b can be configured to generate an electrical signal based on the detected light signal. The electrical signal generated by the photodiodes 126a and 126b is transmitted to the microprocessor 128.

The microprocessor 128 can be an arithmetic and logic unit array. The microprocessor 128 can be provided on a semiconductor substrate and interconnected to the photodiodes 126a and 126b and the antenna 130 for executing operations on received data to generate output data, as described in detail with reference to FIG. 4. The microprocessor 128 can be configured to determine the amount of the fluid within the injection device based at least in part on the electrical signal and transmit the data including the amount of the fluid to the antenna 130 and to the display 136. In some examples, the microprocessor 128 is a microcontroller, e.g., a combination of microprocessor components and other components formed in a single package.

The antenna 130 can be a near-field communication (NFC) antenna having a flexible structure and can be made from a conductive and transparent material configured to maintain the elasticity of the flexible smart label 104. The antenna 130 can be configured to harvest energy for the power source 134. The antenna 130 can be configured to transmit signals to the microprocessor 128 and to an external processor. The signals transmitted by the antenna 130 can include the amount of the fluid in the cartridge 106, the temperature measured by the temperature sensor 132, and the identifier of the flexible smart label 104. The antenna 130 can be configured to transmit data, e.g., at a data rate of 106 kb/s, 212 kb/s or 424 kb/s using Manchester bit encoding and OOK load modulation at e.g., 846 kHz. Each of the plurality of flexible components can be powered by the power source 134. The power source 134 can be an integrated flexible battery or a super capacitor. The power source 134 can be configured to supply energy to the flexible components of the flexible smart label 104 under particular conditions, such as when the fluid delivery system 100 is within an NFC field 160. The NFC field 160 can be generated by an interrogator 162. The interrogator 162 can include a RF module 164, a transmitter 166, a receiver 168, and a processor 170. The interrogator 162 can be configured to communicate with an external device 172 that is configured to display the data received from the flexible smart label 104.

Figure 1C:
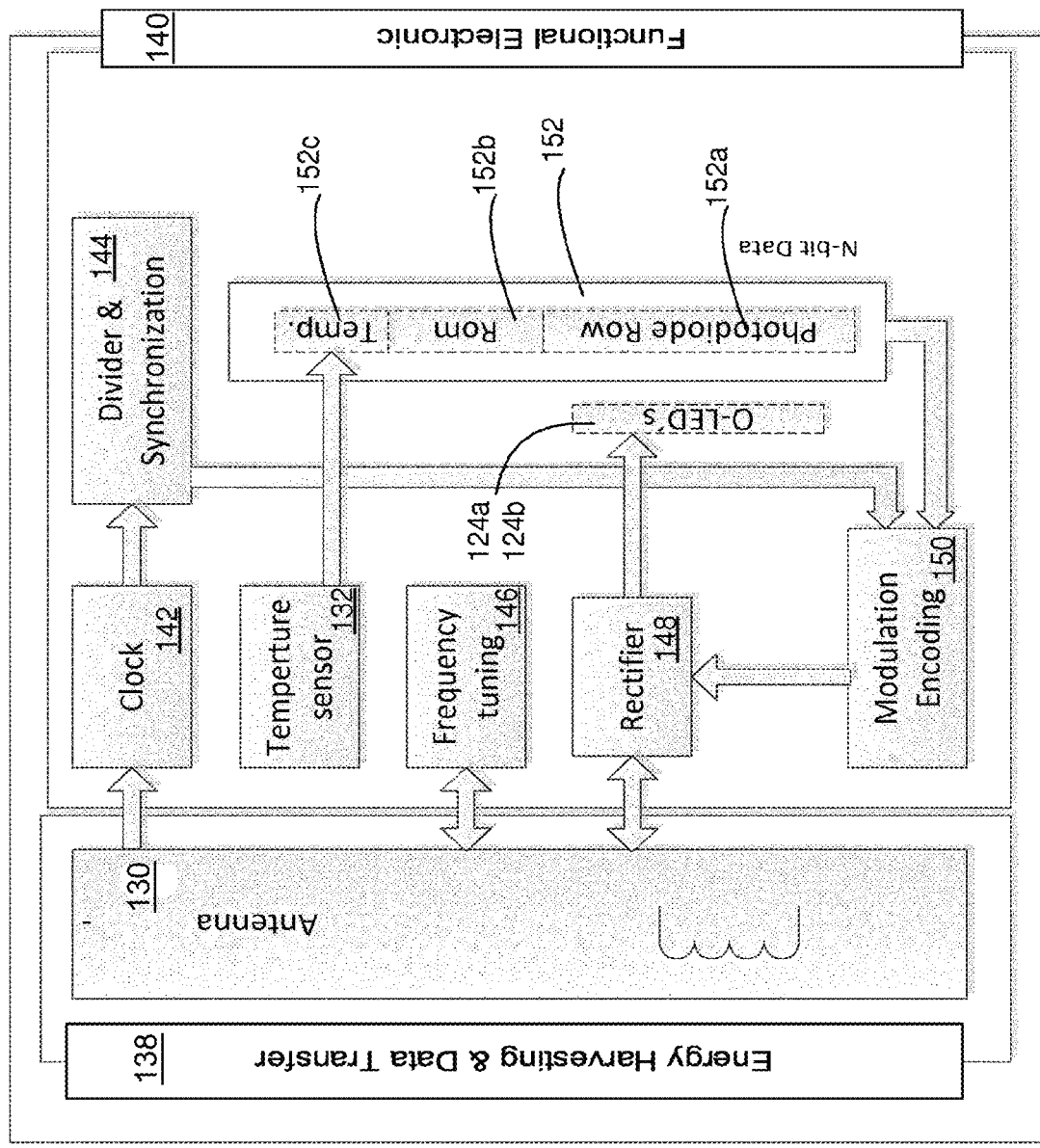
Figure 1D:
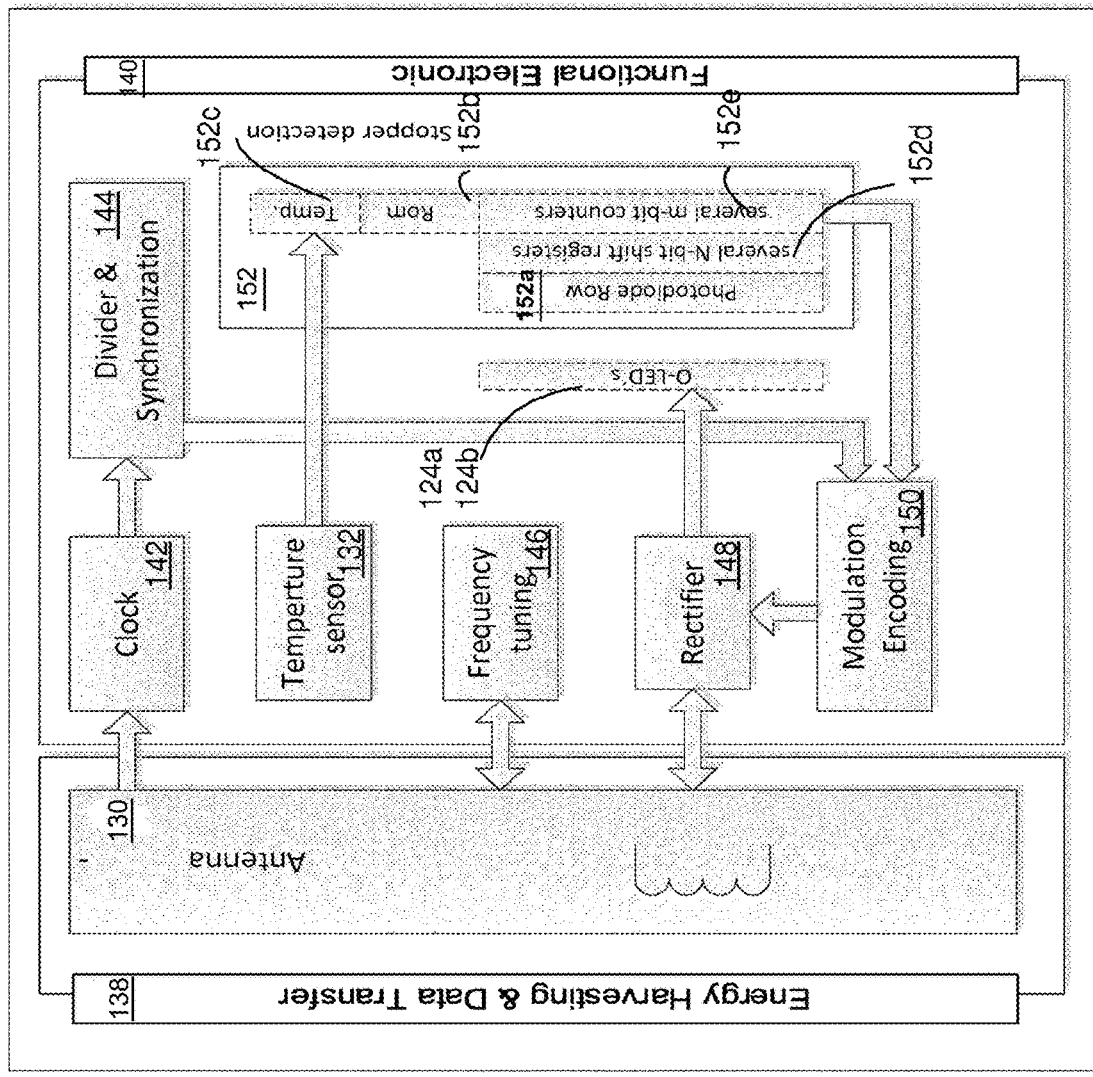
Figure 1E:
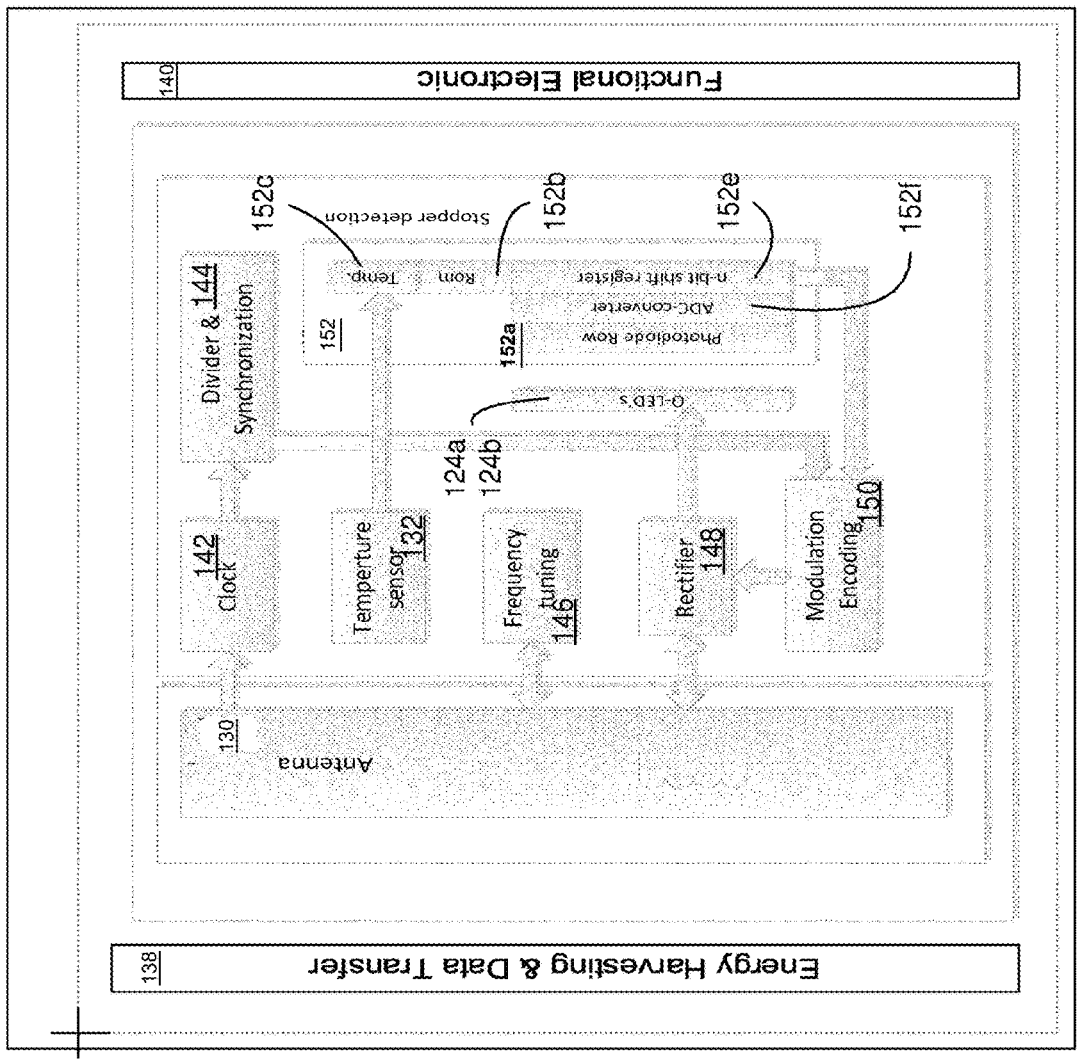

FIGS. 1C and 1D illustrate block diagrams of examples of the flexible smart label 104 in a basic configuration and in a complex configuration including additional digital functions between photodetector and modulation encoding, respectively. The flexible smart label 104 as illustrated in FIGS. 1C, 1D, and 1E can be electronic printed labels. The flexible smart label 104 can provide remote identification and telemetering. The flexible smart label 104 can include an energy harvesting and data transfer module 138 and a functional electronic module 140.

The energy harvesting and data transfer module 138 includes antenna 130, which is mounted within the flexible smart label 104 to receive an exciter signal when being in an NFC field 160. The antenna 130 can receive energy (e.g., radio frequency (RF) energy) from the NFC field 160 (e.g., interrogation field) created by the transmitter 166 in the interrogator 162 of the NFC field 160. In some implementations, through the mechanism of modulated RF backscatter, in which the impedance connected to the antenna 130 may be periodically modulated by an electronic code generator circuit 133 within the smart label 104, the smart label 104 returns part of that energy in the form of a coded reply signal to the receiver 168 in the interrogator 162. The antenna 130 generates a signal to multiple components within functional electronic module 140, such as a clock 142, a frequency tuning module 146, and a rectifier/regulator 148. A signal from the antenna 130 is transmitted to the frequency tuning module 146 to tune the frequency of the antenna 130. A signal from the antenna 130 is transmitted to the clock 142 to generate a clock signal as input for a divider and synchronization module 144. The divider and synchronization module 144 controls the sequencing of the cyclical transmitted data stream for modulation encoding 150, which can modulate the amplitude and/or frequency of the signal before communicating the signal to the rectifier 148.

The rectifier 148 receives the signal from the antenna 130 and converts a portion of the signal received by the antenna 130 to a direct current, for the purposes either of initiating operation of or providing power for the electronic code generating circuits. The unregulated voltage is then regulated to a preset voltage level to power the digital circuitry contained within flexible smart label 104. For example, rectifier 148 limits the voltage to protect the digital electronics and transmits a signal to the LEDS 124a and 124b to generate a light signal.

As illustrated in FIG. 1C, the data 152 generated by the functional electronic module 140 can be an N-bit data including data associated with the electric signal generated by the photodiodes 152a indicating the amount of fluid within the injection device 102, the identifier 152b, and the data generated by the temperature sensor 152c. The electric signal generated by the photodiodes 152a can represent a single drug unit (e.g., indicating that the cartridge is full or empty) or the electric signal can represent a sub portion of a drug unit (e.g., indicating that the cartridge is partially full). In some implementations, and as illustrated in FIG. 1D, the functional electronic module 140 can include additional elements to format the data 152. For example, the data associated with the electric signal generated by the photodiodes 152a can be formatted using digital shift-registers and counters to reduce the amount of data transmitted to a minimum, according to ISO 14443 Type A RFID standard. For example, the electric signal generated by the photodiodes 152a can be formatted as a row pattern that is stored in a several N-bit shift register 152d. In the initial condition the output of the several N-bit shift register 152d can be set to "0." When the antenna 130 detects proximity to NFC field, the antenna supplies pulses to the count-up input of a several-m-bit counter in synchronism with the shift pulses applied to the N-bit shift register 152d to generate formatted data 152e. Using the complex configuration illustrated in FIG. 1D, the data generated by the flexible smart label 104 can include formatted data 152e, the identifier 152b, and the data generated by the temperature sensor 152c. In some implementations, the data 152 can also include a timestamp, a location, and a situation specific data for the injection device 102 (e.g., transportation, storage, or injection of a medicament). In some implementations the photodiode 152a generates an analog output value that is associated with the arrangement of the photodiodes. The data representing the amount of fluid in the cartridge can be determined by performing a transformation of the analog data to digital data 152e by using an analog/digital converter 152f (FIG. 1E) and comparing the amplitude of the digital signal with preset values that correspond to known amounts of fluid within cartridges.

Figure 2:
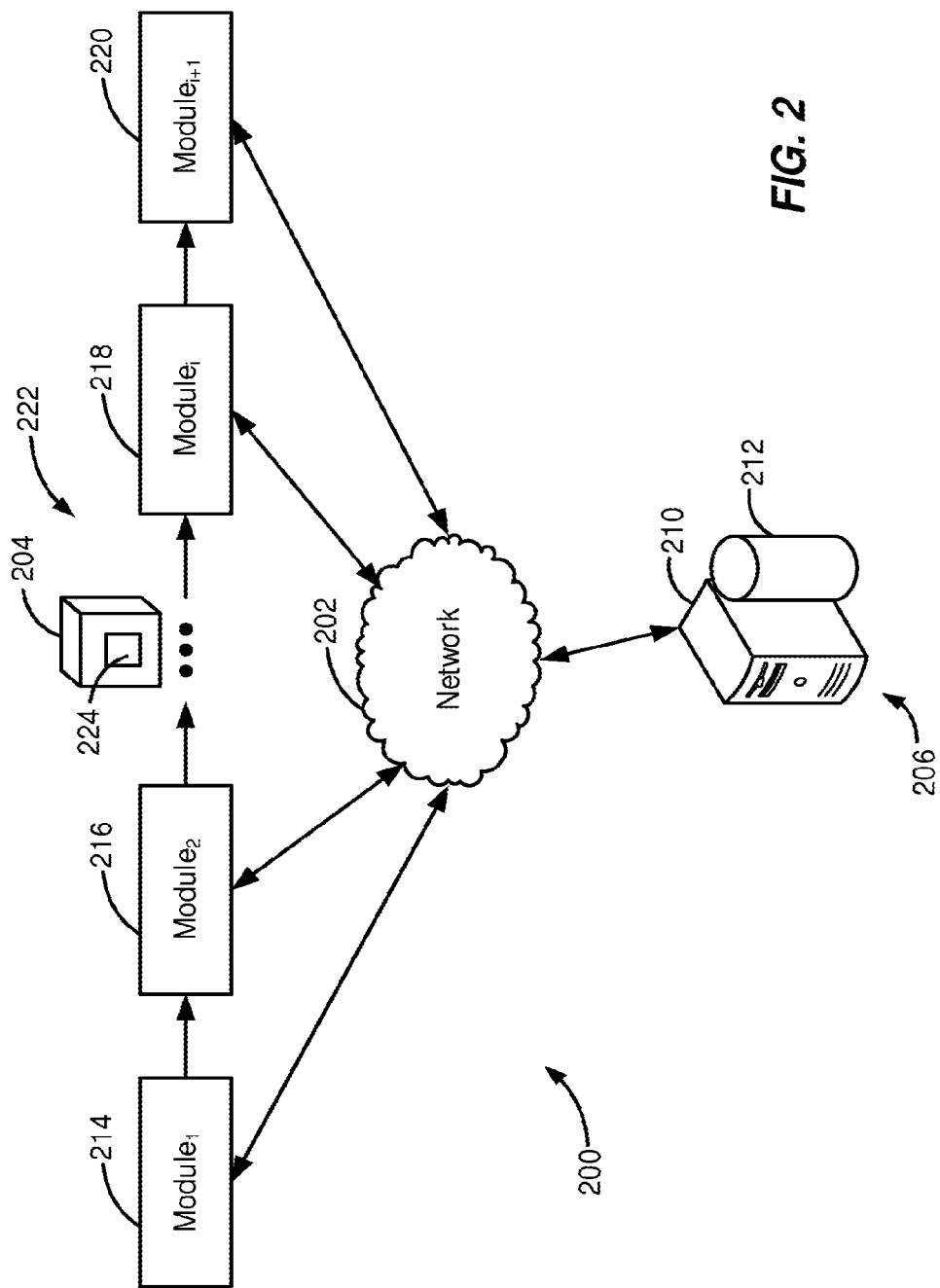
FIG. 2 is a block diagram of an example system architecture that can execute implementations of the present disclosure.

FIG. 2 is a block diagram of an example system 200 that can execute implementations of the present disclosure. The system 200 enables n number of entities (examples of which are entities 214, 216, 218, 220) transfer and access, by way of a network 202, to a central computer 206 that includes a central database 212 and a central server 210.

In the example of FIG. 2, an entity (e.g., entities 214, 216, 218, 220) can be a medicament supplier, a medical facility (e.g., a healthcare provider) or a patient located in a healthcare continuum 222. For example, entity 214 is located before entity 216 in the healthcare continuum 222. Entity 218 is located before entity 220 in the healthcare continuum 222. The healthcare continuum 222 can manufacture, store, transport, and use the item 204. The item 204 along with any additional components (e.g., RFID flexible smart label 224) can be transferred between multiple entities in the healthcare continuum 222 (e.g., from medicament supplier, to healthcare provider working within a medical facility, and to patient) during the medical care process.

The item 204 (e.g., fluid delivery system 100 described with reference to FIGS. 1A and 1B) can include an attached machine-readable medium (e.g., flexible smart label 104 described with reference to FIGS. 1A and 1B). In the illustrated example, the machine-readable medium includes an RFID flexible smart label 224. A unique identification number can be stored on the RFID flexible smart label 224 for the item 204. Each entity along the healthcare continuum 222 can generate and transfer associated item-level data with the item 204 as it is manufactured, transported, stored and used. The item-level data can be associated with the item's unique identification number for storage in the central database 212. One possibility to transfer the item-level data to another device (e.g., the central database 212 of the central computer 206) is similar to an NFC barcode, which adheres to a subset of ISO 14443 Type A RFID standard. The RFID flexible smart label 224 can operate in a read-only Tag-Talks-First (TTF) mode. The item-level data can be transmitted using Manchester bit encoding and on-off keying (OOK) load modulation at e.g., 846 kHz.

In some implementations, the central computer 206 is located at an external service provider. Shared data among entities in the healthcare continuum 222 can be encrypted and stored in the central database 212. Each entity in the healthcare continuum (the n entities in the healthcare continuum 222) can outsource the shared data to the external service provider. In addition, the external service provider can manage access to the stored shared data. For example, the central database 212 may be cloud storage and the central computer 206 may be a cloud computing system hosted by a third party or service provider. The cloud storage service provider can manage and maintain the central database 212 where the entities 214, 216, 218, 220 can store item-level data for sharing and exchanging among the entities 214, 216, 218, 220.

Each entity (e.g., entities 214, 216, 218, 220) can encrypt and store item-level data for an item used by the healthcare continuum 222 in the usage of the product 204 (e.g., in association with injection of a medicament) in the central database 212. The central database 212 can include a unique identification number for each item and one or more tuples for the item where each tuple includes item-level data provided by an entity in the healthcare continuum. In some implementations, a random number "r" included in the RFID flexible smart label (described with reference to FIG. 2) or 2D bar code for the item can be the item's identification number. The identification number can be used as an index into the database that includes all of the item-level data for the item.

Each entity in the healthcare continuum (the n entities in the healthcare continuum 222) can outsource their encrypted item-level data to the external service provider. The entity (e.g., patient and/or healthcare provider) that owns the medical data can manage the access to the encrypted data by other entities (e.g., medicament supplier) as well as the service provider by using and maintaining encryption keys. This can allow entities the ability to provide an encryption scheme related to outsourced database security and searchable encryption that can be used by multiple entities and service providers.

Security requirements for the central database 212 can prevent a party observing the central database 212 from tracking items in the central database 212. The security requirements can prevent an attacker that continuously monitors the central database 212 from determining any information with regard to the data stored in the central database 212. In addition, the entity that owns the data (the data owner) included in the central database 212 can enforce various levels of access control to the item-level data for its items. For example, regarding item 204, the data owner (e.g., patient) can provide access control to item-level data for item 204 to another entity (e.g., healthcare provider) based on the association with the other entity.

In some implementations, a patient can provide individual access to a physician for each tuple of item-level data stored for the item 204 in the central database 212. The data access control allows the patient to set the access level to each individual tuple of the item-level data. In some implementations, a healthcare administrator can provide a healthcare provider access to all tuples of item-level data for an item that a medical facility possessed at one time. For example, a healthcare administrator can use the access control for item-level tracking. The healthcare administrator can allow or restrict the visibility of items on an item-by-item basis to other entities that at one time may have had possession of the item or may have been associated with the item (e.g., only healthcare providers associated with a particular type of medical treatment delivered to corresponding patients would be granted access to the data). This can allow one entity (e.g., the healthcare administrator) to provide item-level data access to other entities without having to set individually the access control of each tuple of the item-level data to each individual entity. For example, entities, including the healthcare administrator, may then engage in fair data sharing agreements for an item with one another without the risk of disclosing sensitive or confidential information, either directly or by inference, regarding each individual item or entity.

In some implementations, a healthcare administrator or a patient can provide an entity access to all tuples of item-level data. For example, the entity can be a trusted third party (e.g., a patient, a healthcare provider, a medicament supplier or other third parties) full access to all tuples of the item-level data. In the case where the central database 212 may be cloud storage and the central computer 206 may be a cloud computing system hosted by a third party or service provider, the access level may be used between the healthcare administrator or the patient and the service provider in order for the service provider to manage and maintain the central database 212 and provide automatic refills based on the data generated by the flexible smart label 224.

Each entity can utilize cryptographic processes and algorithms to enable the secure handling of item-level data among entities. Cryptography involves the design and analysis of mathematical techniques that can enable secure communications in the presence of malicious adversaries. The use of cryptographic processes and algorithms by a data owner can prevent unwanted entities from accessing item-level data stored in a central repository. In some implementations, symmetrical encryption can involve communicating entities to agree on secret and authentic keying material for use in encrypting and decrypting data exchanged between the communicating entities. For example, symmetrical encryption can be used for each tuple of data exchanged between the communicating entities. In some implementations, asymmetrical encryption can use a public-key scheme where communicating entities exchange keying material that is authentic but not secret. Each entity selects a single key pair that includes the public key and a related private key kept secret by the entity. A key pair can be associated with each tuple of data exchanged between entities. The use of symmetrical and asymmetrical encryption, as described, assumes a key or key pair for each tuple for each entity. Entities, when sharing data, would exchange a key or key pair for each tuple of data shared. For example, a healthcare continuum may produce millions of items utilizing hundreds of healthcare continuum partners (entities) resulting in the use of a large number of cryptographic keys, as a cryptographic key for each tuple would be exchanged between entities for each entity.

In some implementations, and in order to reduce the number of cryptographic keys while enabling the secure handling of item-level data among entities, a cryptographic scheme can use a random number r as a unique identifier for an item along with two cryptographic keys. Communicating entities can perform a one-time exchange of cryptographic keys where new or additional items or tuples would not need an exchange of new cryptographic keys between the communicating entities. In addition, the encrypted item-level data can be stored in a central repository accessible by both trusted and untrusted entities, but protected from access by any untrusted entities and even the third party service provider.

Each flexible smart label can be associated with an identifier. For example, a random number r may be encoded in a machine-readable medium, such as radio frequency identification (RFID) data, in a 2-dimensional (2D) bar code, and/or in a QR code included with the item. The random number r can be associated with a particular flexible smart label and can be used to uniquely identify the flexible smart label and corresponding flexible smart label-level data stored in a repository. In some cases, health regulation compliance or best business practices may be inferred by the sharing of the flexible smart label-level data across healthcare continuum where one medical entity has no control over the other medical entities (e.g., healthcare provider or patient) that may have access to their flexible smart label data.

The use of item-level tracking by a medical entity for flexible smart labels in their healthcare continuum may allow the medical entity to collect information regarding a fluid to be injected with the injection device from the machine-readable medium (e.g., by scanning an RFID flexible smart label). The machine-readable medium can provide a sequence of elements that include a unique identifier for the flexible smart label, an amount of fluid within a cartridge and/or injection device, a timestamp, a location, and a situation specific data for the injection device to which the flexible smart label is attached. The medical entity can record or store the elements in a "tuple" as item-level data in a data repository for the healthcare provider. In some implementations, the data repository can be located within a medical facility. In some implementations, the data repository can be located outside of the medical facility. For example, the data can be stored in a data repository provided by a cloud service provider. In these implementations, the healthcare provider can enforce access control to a part or all flexible smart label data for particular entities in the healthcare continuum. Entities in the healthcare continuum sharing data may need to gain access to data provided by multiple healthcare providers. In implementations including a cloud service provider, the flexible smart label data of the multiple healthcare providers can be stored in a central data repository provided in the cloud.

Accordingly, and in some implementations, healthcare providers in a healthcare continuum can share a common database for use as a central repository for item-level data. A service provider or third party may manage the resources of the shared central repository. When using a central shared repository, the healthcare provider that owns the flexible smart label data may no longer be able to control access to its data. Sharing a common database among healthcare providers in a healthcare continuum can improve database query performance when a healthcare provider gathers item-level data for a large number of flexible smart labels. However, sharing a common database may introduce security issues, as each healthcare provider may want to monitor and control access to the flexible smart label data it owns and at least partially block the access of other entities in the healthcare continuum that do not own the data.

In some implementations, a healthcare provider may encrypt flexible smart label data stored in a central repository for exchange with other entities in a healthcare continuum. The encrypted flexible smart label data may be stored in a central repository accessible by all healthcare providers. For example, the central repository may be a cloud storage included in a cloud computing system hosted by a third party or service provider. The cloud storage service provider can manage and maintain a central repository where multiple healthcare providers and entities can store their flexible smart label data for sharing with and access by other entities. Encrypting the flexible smart label data stored in a cloud-based data repository allows the data owner to determine and enforce access control to their stored flexible smart label data as only healthcare providers or other public entities that have knowledge of a private key for use in decrypting the flexible smart label data will be able to read the flexible smart label data stored in the cloud-based data repository. In some implementations, the service provider may not know the private key. As such, the service provider would not be able to decrypt the data and additionally would not be able to distribute the private key, intentionally or unintentionally, to any companies or other public entities thereby maintaining the confidentiality of the stored item-level data.

Sharing and exchanging of flexible smart label data among medical facilities in the healthcare continuum can enable the use of various applications for analysis of the data. For example, anti-counterfeiting applications, healthcare continuum bench marking applications and applications that identify compliance with healthcare rules and regulations can use the shared flexible smart label data to provide information to the healthcare providers and/or entities in the healthcare continuum.

Figure 3:
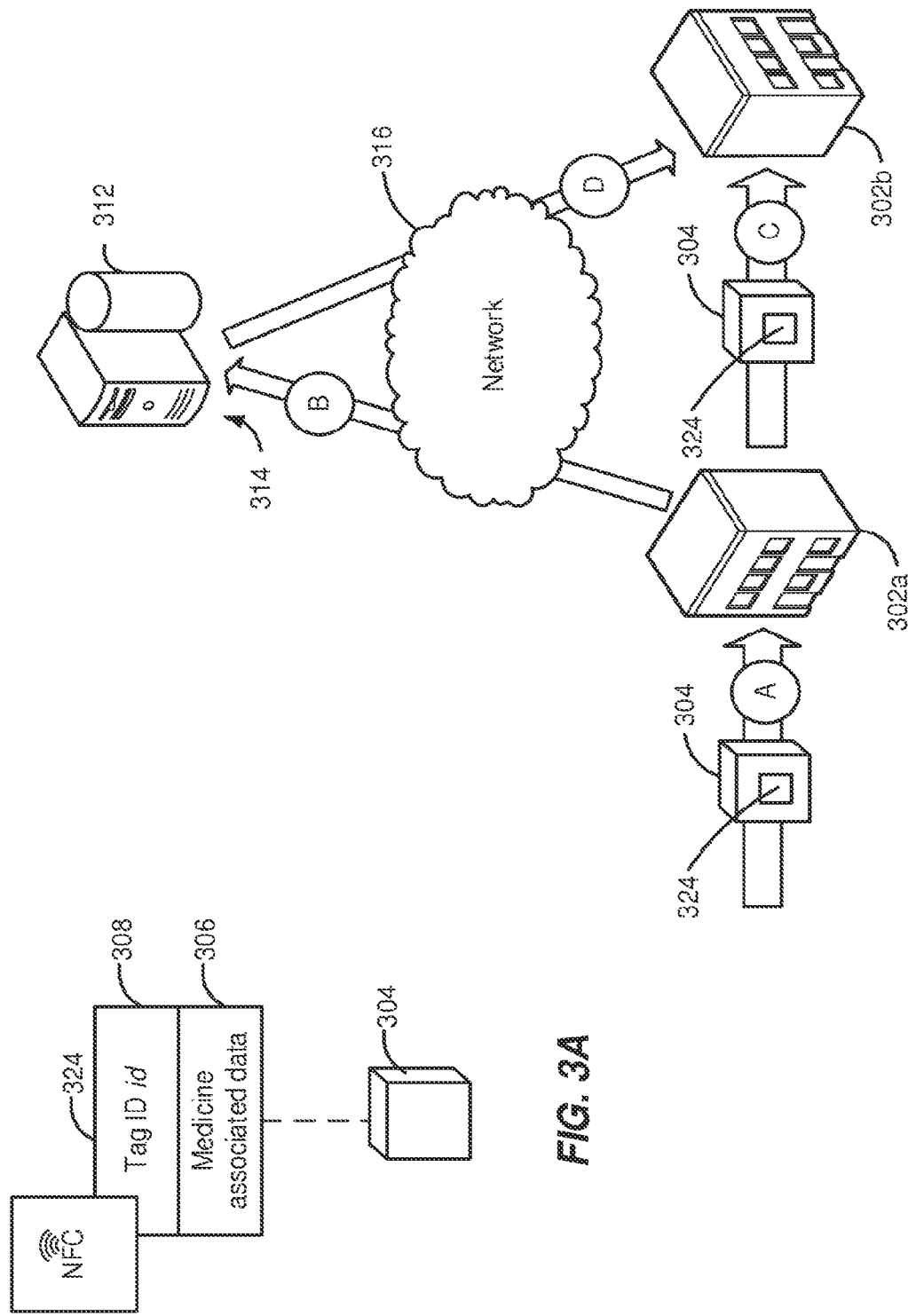
FIGS. 3A and 3B are diagrams depicting data sharing in accordance with the present disclosure.

FIG. 3A is a diagram of example data that can be provided from a machine-readable medium (e.g., RFID flexible smart label 104 described with reference to FIGS. 1A-1D) associated with an item 304 (e.g., injection device 102 described with reference to FIGS. 1A and 1B). The RFID flexible smart label 124 can include a unique smart label identifier id 308 that can remain unchanged throughout the healthcare continuum and medicine associated data 306 (e.g., data 152 as described with reference to FIGS. 1C and 1D) that can change throughout the healthcare continuum with changes in storage temperature conditions and variations in the amount of medicine contained within the item 304.

The unique smart label identifier id 308 includes a random number r that can be a unique number associated with the item 304. For example, the random number r can be written to the RFID flexible smart label 324 during or after the manufacturing process. An entity in possession of the item 304 can access and read the unique smart label identifier id 308, for example, when being within NFC field and use the item 304, for example, to inject an amount of medicine, which changes the medicine associated data 306. During after manufacturing, during transportation, during storage, and during usage processes, medicine associated data 306 (e.g., including the data types described with reference to FIGS. 1C and 1D) can be accumulated throughout the healthcare continuum. Each entity along the healthcare continuum can store the medicine associated data 306 accumulated during the value added step performed by the entity in the healthcare continuum as item-level data.

In some implementations, the item 304 can include a non-electronic tracking method. In these implementations, a unique identifier for the item 304 can also be a random number r associated with the item 304 and encoded in the non-electronic tracking method. Tuples (I, D) in a cryptographic scheme can include two values: a unique identifier, I, representative of the combination of one item with one entity, and encrypted item-level data D. The unique identifier, I, for the item can be used to locate and identify the encrypted data D within the central repository. For example, the unique identifier, I, can be used as an index to a data table of encrypted item-level data included in a database or central repository. The unique identifier, I, can be used to query for the encrypted data D, from the central repository.

FIG. 3B is a diagram depicting example steps for secure sharing of item-level medicine associated data 306 in accordance with the present disclosure. For example, a company 302a receives or produces the item 304 that includes the RFID flexible smart label 324. The company 302a collects item-level data regarding the item 304, such as medicine manufacture date and expiration date (arrow A). The company 302a can be configured to be within a NFC region, such that company 302a can automatically update item-level data regarding the item 304. For example, company 302a can store the item 304 at a particular temperature for a particular duration of time, the storage conditions can be included in updated data related to the item 304. The collected data and the updated data can be encrypted and sent over network 316 for storage from company 302a to a central database 312 of the central computer 314 (arrow B) in the form of tuples (I, D).

The company 302a can sell and/or send the item 304 to a company 302b (arrow C). The company 302b can be configured to be within a NFC region, such that company 302b can use flexible smart label 324 to read current item data (e.g., unique smart label identifier id 308 and medicine associate data 306, such as amount of fluid contained within the item 304). The company 302b can use the item data (e.g., unique smart label identifier id 308) to query for and decrypt the item-level data 306 and 308 stored in the central database 312 of the central computer 314 by company 302a (arrow D) and. For example, company 302b can verify an expiration date of the medicine and previous storage conditions, such as temperature during storage. The company 302b can be configured to automatically update medicine associated data 306, including data associated with storage conditions and variations in the amount of fluid contained within the item 304.

Figure 4:
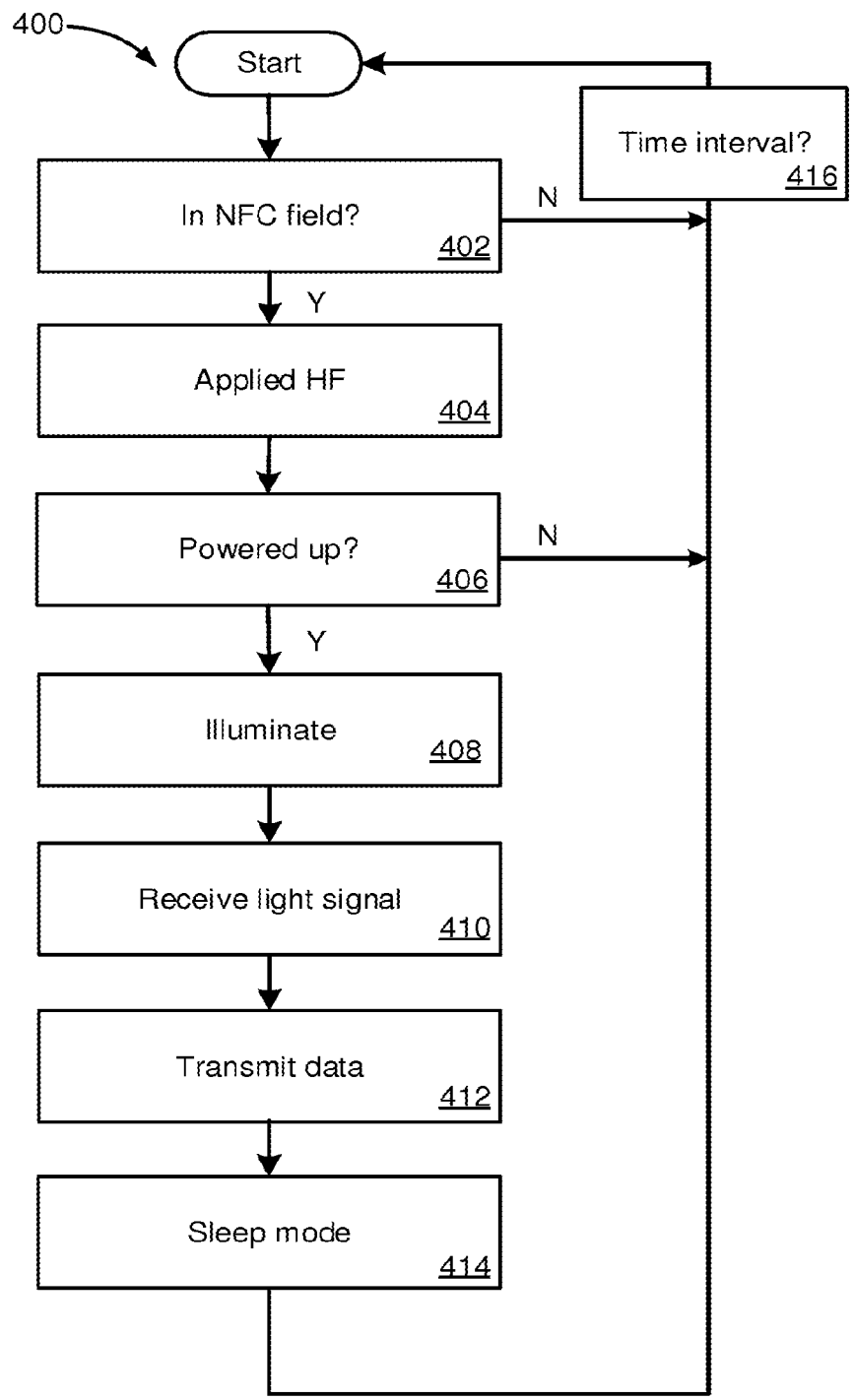
FIG. 4 is a flowchart illustrating an example process that can be executed to encrypt item-level data for storage in a central database.

FIG. 4 is a flowchart illustrating an example process 400 that can be executed to encrypt item-level data for storage in a central database. The process 400 can be executed by devices and systems described with reference to FIGS. 1, 2, and 3. The process 400 begins by identifying whether an item is within a NFC region (402). For example, the item can be configured to periodically verify its proximity to an NFC region. The item can be an injection device, having a flexible smart label that includes one or more components configured to verify the proximity of the injection device to an NFC region. A healthcare provider can store and use the injection device while being within a medical facility configured to be within a NFC region.

In response to determining that the item is within a NFC region, the item determines whether a high frequency signal is applied (404). In some implementations, a high frequency signal is automatically generated in response to a usage of the item. For example, a high frequency signal is automatically generated after the injection device was used to inject an amount of the medicine contained within the injection device.

In response to determining that the high frequency signal is applied the item can be powered up (406). For example, in preparing to generate an updated data associated with the item, one or more electronic components of the flexible smart label are energized (as described with reference to FIGS. 1A-1D) using a power source integrated within the flexible smart label. In case the power source is depleted of energy, the power source can recharge while the item is in the NFC region and process 400 can restart.

In response to one or more components of the item being powered up, a light source, such as LEDS 124a and 124b, can illuminate a target (408), as described with reference to FIGS. 1A and 1B. A receiver, such as photodiodes 126a and 126b, can detect at least a portion of the light signal and generate a data associated with the detected portion of the light signal (410). For example, the portion of the light signal detected by the photodiodes can indicate the stopper position, which can be used to determine the amount of the fluid within the injection device based on known geometrical characteristics of the injection device and cartridge. The item can be configured to transmit the data to a database, such as central database 312 described with reference to FIG. 3B (412). In response to successful transmission of data, the item can initiate sleep mode to conserve the energy of the power source (414). In some implementations, the item is configured to periodically restart the process based on a preset time interval (416).

Figure 5:
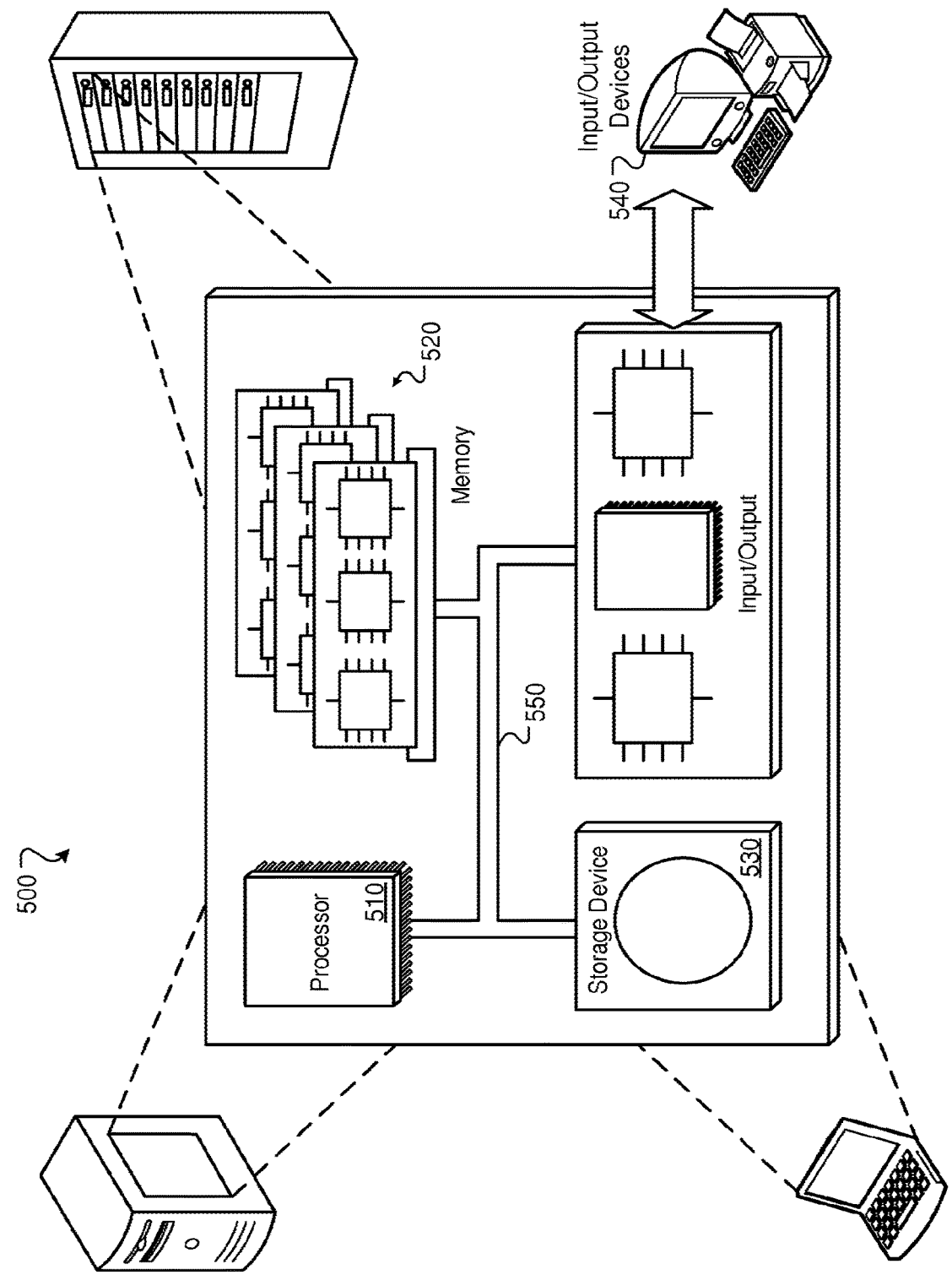
FIG. 5 is a schematic illustration of example computer systems that can be used to execute implementations of the present disclosure.

Referring now to FIG. 5, a schematic diagram of an example computing system 500 is provided. The system 500 can be used for the operations described in association with the implementations described herein. For example, the system 500 may be included in any or all of the server components discussed herein. The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit. The storage device 530 is capable of providing mass storage for the system 500. In one implementation, the storage device 530 is a computer-readable medium. In various different implementations, the storage device 530 may be a floppy disk device, a hard disk device, an optical disk device, or a tape device. The input/output device 540 provides input/output operations for the system 500. In one implementation, the input/output device 540 includes a keyboard and/or pointing device. In another implementation, the input/output device 540 includes a display unit for displaying graphical user interfaces that enable a user to access data related to an item that is collected, stored and queried as described with reference to FIGS. 1-4.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(w-carboxyheptadecanoyl)-des(B30) human insulin and B29-N-(w-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SUP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted 06-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals)

of various components of the substances, formulations, apparatuses, methods, systems, devices, and embodiments described herein may be made without departing from the full scope and spirit of the present inventive concepts, which encompass such modifications and any equivalents thereof.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor, and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files, such devices include magnetic disks, such as internal hard disks and removable disks, magneto-optical disks, and optical disks. Storage devices suitable for tangibly embodying computer program instructions and data include all forms of non-volatile memory, including by way of example semiconductor memory devices, such as EPROM, EEPROM, and flash memory devices, magnetic disks such as internal hard disks and removable disks, magneto-optical disks, and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. A method of operating a module associated with an auto injector, the method comprising:
   determining that the module is in a near-field communication (NFC) region;
   in response to the determining, retrieving, from a memory of the module, data associated with a medicament contained in the auto injector, the medicament comprising antibodies selected from the group consisting of: anti PCSK-9, anti IL-6 mAb, and anti IL-4 mAb; and
   transmitting the data associated with the medicament from an antenna of the module to an external device in the NFC region,
   wherein the module is configured to attach to the auto injector through an adhesive layer of the module.

2. The method of claim 1, further comprising powering up one or more electronic components of the module in response to determining that the module is in the NFC region.

3. The method of claim 1, further comprising encrypting the data associated with the medicament.

4. The method of claim 1, further comprising decrypting the data associated with the medicament.

5. The method of claim 1, further comprising transmitting an identification number of the module from the antenna of the module to the external device.

6. The method of claim 5, further comprising storing the data associated with the medicament and the identification number of the module in a memory of the external device.

7. The method of claim 1, further comprising storing the data that was transmitted from the module to the external device in a memory of the external device.

8. The method of claim 7, wherein the data is stored in the memory of the external device in form of one or more tuples.

9. The method of claim 1, further comprising:
   receiving, from the external device, updated data associated with the medicament; and
   storing the updated data in the memory of the module.

10. The method of claim 1, wherein the module is a flexible module, and the antenna is
    a near-field communication (NFC) antenna having a structure configured to maintain an elasticity of the flexible module, and wherein the data associated with the medicament is indicative of an amount of the medicament contained in the auto injector.

11. The method of claim 1, further comprising determining an authenticity of the medicament based on at least the data associated with the medicament.

12. A method comprising:
transmitting, to an antenna of a flexible module that is associated with an auto injector, data associated with a medicament contained in the auto injector, the medicament comprising antibodies selected from the group consisting of: anti PCSK-9, anti IL-6 mAb, and anti IL-4 mAb; and
storing the data associated with the medicament in a memory of the flexible module,
wherein the antenna and the memory are included in a flexible carrier layer of the flexible module, the flexible carrier layer being configured to be attached to at least one portion of a surface of the auto injector by an adhesive layer of the flexible module.

13. The method of claim 12, wherein the data associated with the medicament is indicative of an expiration date of the medicament.

14. The method of claim 12, wherein the data associated with the medicament is indicative of a usage of the medicament through the auto injector.

15. The method of claim 12, wherein the data associated with the medicament is indicative of a manufacture date of the medicament.

16. The method of claim 12, wherein the data associated with the medicament is indicative of an amount of the medicament contained within the auto injector.

17. The method of claim 12, wherein the data associated with the medicament is indicative of an identity of the medicament.

18. The method of claim 12, further comprising attaching the flexible carrier layer to the at least one portion of the surface of the auto injector.

19. A method comprising:
storing, on a memory of a flexible module that is associated with an auto injector, data associated with a medicament contained in the auto injector,
wherein the memory is included in a flexible carrier layer of the flexible module, the flexible carrier layer being configured to be attached to at least one portion of a surface of the auto injector by an adhesive layer of the flexible module, and
wherein the medicament comprises one or more antibodies.

20. The method of claim 19, wherein the data associated with the medicament includes at least one of an expiration date of the medicament, a manufacturing date of the medicament, information of a usage of the medicament through the auto injector, an amount of the medicament contained within the auto injector, or an identity of the medicament.

* * * * *